United States Patent
Tsuruta

(10) Patent No.: US 10,769,737 B2
(45) Date of Patent: Sep. 8, 2020

(54) INFORMATION PROCESSING DEVICE, INFORMATION PROCESSING METHOD, AND PROGRAM

(71) Applicant: SONY CORPORATION, Tokyo (JP)

(72) Inventor: Yasushi Tsuruta, Tokyo (JP)

(73) Assignee: SONY CORPORATION, Tokyo (JP)

( * ) Notice: Subject to any disclaimer, the term of this patent is extended or adjusted under 35 U.S.C. 154(b) by 134 days.

(21) Appl. No.: 15/558,601

(22) PCT Filed: Feb. 24, 2016

(86) PCT No.: PCT/JP2016/055414
§ 371 (c)(1),
(2) Date: Sep. 15, 2017

(87) PCT Pub. No.: WO2016/189908
PCT Pub. Date: Dec. 1, 2016

(65) Prior Publication Data
US 2018/0082387 A1    Mar. 22, 2018

(30) Foreign Application Priority Data

May 27, 2015  (JP) ................................ 2015-107821

(51) Int. Cl.
*G06Q 50/16*         (2012.01)
*G06F 16/29*         (2019.01)
(Continued)

(52) U.S. Cl.
CPC ............ *G06Q 50/16* (2013.01); *A61B 5/1118* (2013.01); *G06F 16/00* (2019.01); *G06F 16/29* (2019.01);
(Continued)

(58) Field of Classification Search
CPC ....... G06Q 50/16; G06F 16/00; A61B 5/1118; G06K 9/00302; G06K 9/00315; G06K 9/00335; G10L 25/63; H04W 4/02
(Continued)

(56) References Cited

U.S. PATENT DOCUMENTS

2002/0083025 A1*  6/2002  Robarts .................. G06F 1/163
                                                           706/12
2004/0230452 A1    11/2004  Abe et al.
(Continued)

FOREIGN PATENT DOCUMENTS

JP    2003-323483 A    11/2003
JP    2004-171079 A     6/2004
(Continued)

OTHER PUBLICATIONS

BBC Magazine, "The curious story of how the lie detector came to be," [online], published on May 21, 2013, available at: < https://www.bbc.com/news/magazine-22467640 > last accessed Dec. 19, 2019 (Year: 2013).*

(Continued)

*Primary Examiner* — Dennis W Ruhl
*Assistant Examiner* — Richard W. Crandall
(74) *Attorney, Agent, or Firm* — Xsensus LLP

(57) ABSTRACT

[Object] To provide an information processing device, an information processing method, and a program capable of providing property transactions with a higher degree of satisfaction by generating certain property information using a happiness score based on user information.
[Solution] The information processing device includes: a computation unit that computes a happiness score on a basis of sensed user information; and a generation unit that generates certain property information using the computed happiness score.

20 Claims, 10 Drawing Sheets

(51) Int. Cl.
*G06F 16/00* (2019.01)
*G10L 25/63* (2013.01)
*A61B 5/11* (2006.01)
*G06K 9/00* (2006.01)

(52) U.S. Cl.
CPC .......... *G06K 9/00302* (2013.01); *G10L 25/63* (2013.01)

(58) Field of Classification Search
USPC ........................................................ 705/313
See application file for complete search history.

(56) References Cited

U.S. PATENT DOCUMENTS

| | | | | |
|---|---|---|---|---|
| 2006/0111923 | A1* | 5/2006 | Elslager | G06Q 50/16 705/1.1 |
| 2009/0048938 | A1* | 2/2009 | Dupray | G06Q 30/02 705/27.1 |
| 2009/0079547 | A1* | 3/2009 | Oksanen | G06Q 30/02 340/10.3 |
| 2012/0158748 | A1* | 6/2012 | Smintina | G06Q 50/16 707/748 |
| 2013/0143185 | A1* | 6/2013 | Liu | G09B 19/00 434/236 |
| 2014/0280529 | A1* | 9/2014 | Davis | A61B 5/0022 709/204 |
| 2015/0169832 | A1* | 6/2015 | Davis | H04M 1/72569 702/19 |

FOREIGN PATENT DOCUMENTS

| | | | |
|---|---|---|---|
| JP | 2004-178237 A | 6/2004 | |
| JP | 2004-341763 A | 12/2004 | |
| JP | 2007-79478 A | 3/2007 | |
| WO | WO-2014074426 A1 * | 5/2014 | ......... G06Q 30/0242 |

OTHER PUBLICATIONS

Larson, John A., Modification of the Marston Deception Test, 12 J. Am. Inst. Crim. L. & Criminology 390, published 1922 (Year: 1922).*

Chen, Yen-Shen, "Emotion Management and High Interactivity Video Games: Examining Emotion Change in Relation to Arousal, Involvement, and Enjoyment," dissertation, The Florida State University College of Communication and Information, 2010 (Year: 2010).*

Crits-Christoph, Paul Frank, "The Role of Anger in High Blood Pressure," dissertation, Yale University, 1984 (Year: 1984).*

Parker, William Robert, "An Experimental Study of Certain Physiological, Introspective and Rating-Scale Techniques for the Measurement of Stage Fright," dissertation, University of Southern California, 1951 (Year: 1951).*

Bekiempis, Victoria, "Nearly 1 in 5 Americans Suffers from Mental Illness Each Year," Newsweek, Feb. 28, 2014, available at: <https://www.newsweek.com/nearly-1-5-americans-suffer-mental-illness-each-year-230608> (Year: 2014).*

International Search Report dated Mar. 29, 2016 in PCT/JP2016/055414.

* cited by examiner

🏠 EDIT PROPERTY CONDITIONS

RENT

1110 — [NO LOWER LIMIT ▼] ~ [UP TO ¥100,000 ▼]

☐ ADMINISTRATIVE AND OTHER FEES INCLUDED
☐ NO DEPOSIT/KEY MONEY

PROPERTY TYPE

1120 — ☑ HIGH-RISE   ☐ APARTMENT
☐ DETACHED HOUSE

LAYOUT

1130 —
☐ 1R   ☑ 1K   ☐ 1DK
☐ 1LDK   ☐ 2K   ☐ 2DK
☐ 2LDK   ☐ 3K   ☐ 3DK
☐ 3LDK   ☐ 4K   ☐ 4DK
☐ 4LDK   ☐ 5DK
☐ 5LDK OR LARGER

EXCLUSIVELY-OWNED AREA

1140 — [AT LEAST 30m² ▼]

HAPPINESS SCORE

1150 — [AT LEAST 70 ▼]

FIG. 6

| TRANSPORTATION (RAIL LINE/STATION/ BUS STOP) ▲▼ | BUS WALK ▲▼ | LOCATION ▲▼ | RENT ADMINISTRATIVE/ OTHER FEES ▲▼ | KEY MONEY/ DEPOSIT SECURITY DEPOSIT RESTORATION FEE | LAYOUT SIZE ▲▼ | PROPERTY TYPE CONSTRUCTION DATE ▲▼ | HAPPINESS SCORE ▲▼ |
|---|---|---|---|---|---|---|---|
| AA LINE, BB STATION 🏠 REAL ESTATE COMPANY E | — 10 MIN. | 00-CHOME, JJ-KU | ¥80,000 ¥10,000 | 1 MONTH/NONE NONE — | 1K 22.56m² | RENTAL HIGH-RISE UNIT FEB. '04 | 91 |
| AA LINE, CC STATION 🏠 REAL ESTATE COMPANY F | — 7 MIN. | 00-CHOME, KK-KU | ¥81,000 ¥3,000 | 1 MONTH/ 2 MONTHS NONE — | 1K 19.91m² | RENTAL APARTMENT MAR. '77 | 81 |
| AA LINE, CC STATION 🏠 REAL ESTATE COMPANY G | — 7 MIN. | 00-CHOME, KK-KU | ¥81,000 ¥3,000 | 1 MONTH/ 2 MONTHS NONE — | 1K 19.91m² | RENTAL APARTMENT MAR. '77 | 72 |

1200, 1210, 1220, 1230

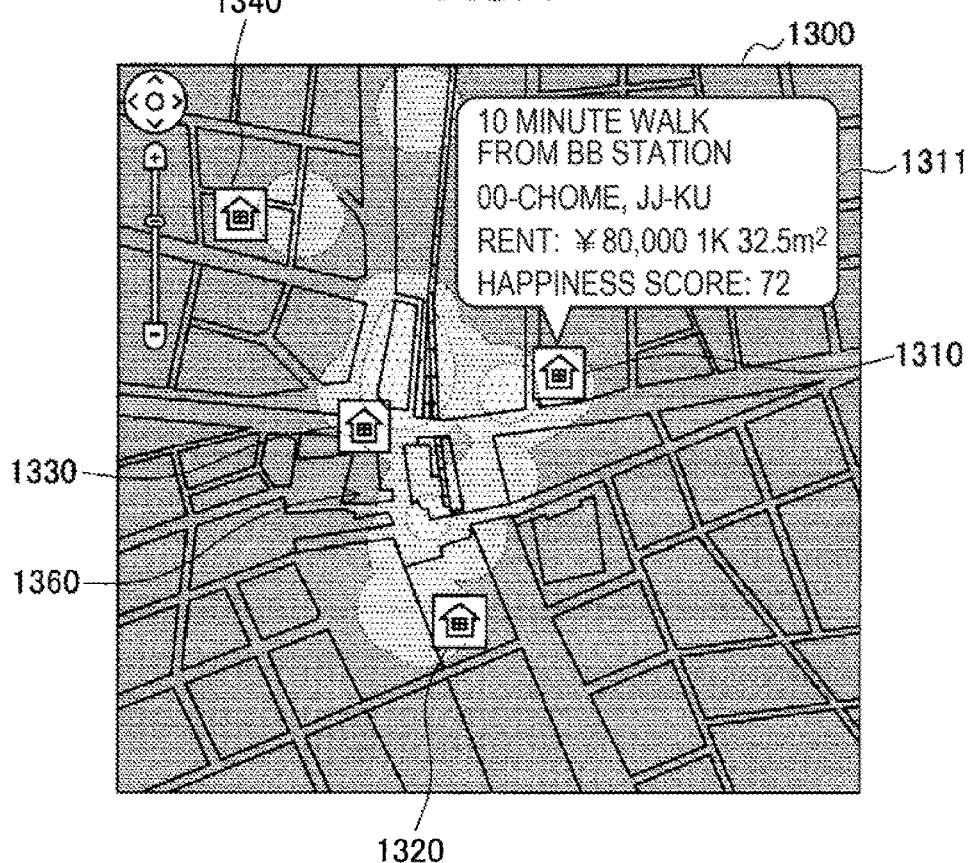

FIG. 9

PROPERTIES WITH HAPPINESS CLOSE TO SELECTED PROPERTY

CC STATION
¥ 87,000
SEE DETAILS
1510

DD STATION
¥ 90,000
SEE DETAILS
1520

DD STATION
¥ 50,000
SEE DETAILS
1530

1500

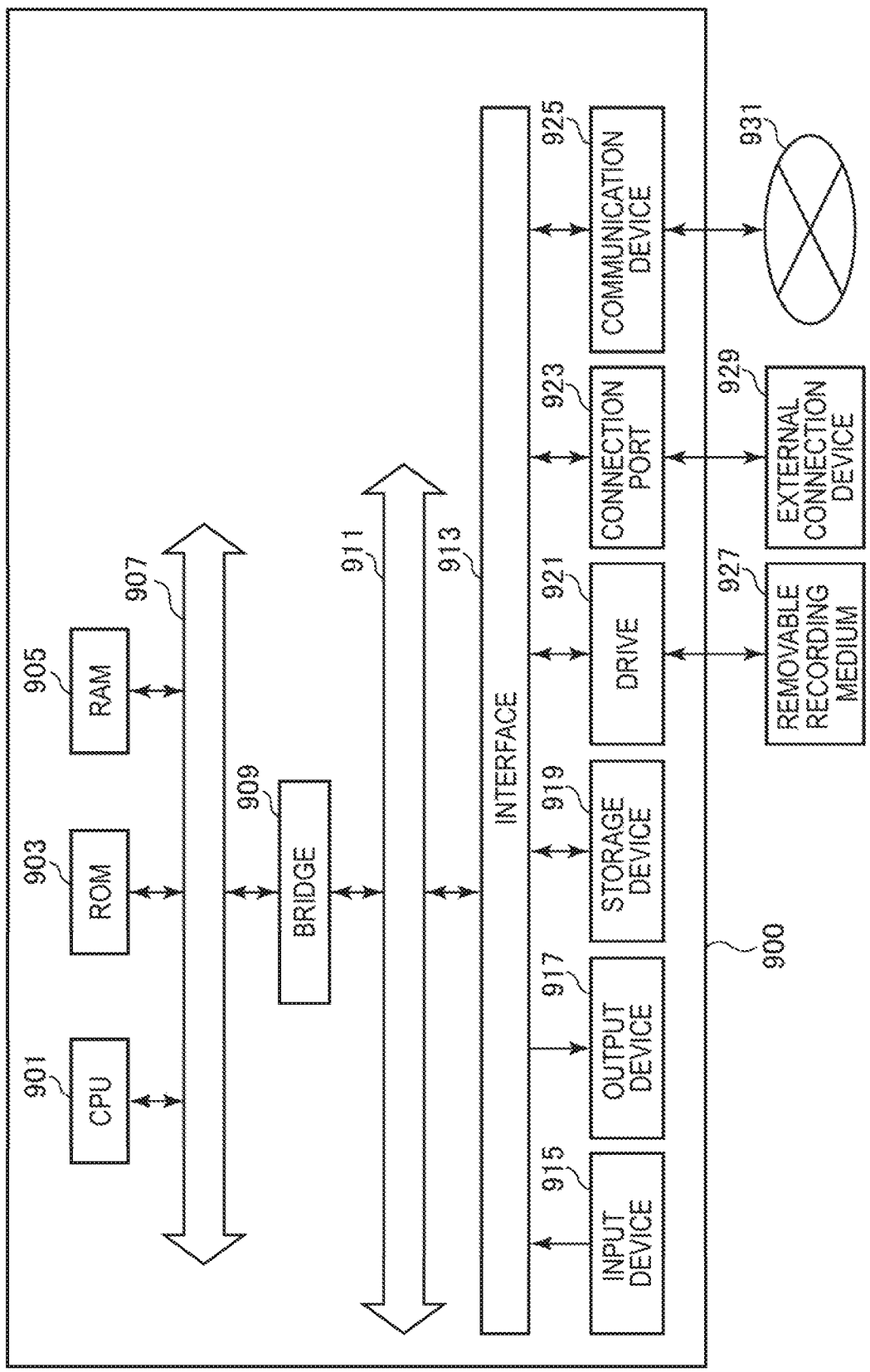

INFORMATION PROCESSING DEVICE, INFORMATION PROCESSING METHOD, AND PROGRAM

TECHNICAL FIELD

The present disclosure relates to an information processing device, an information processing method, and a program.

BACKGROUND ART

Recently, even in real estate transactions, actions such as information searches and correspondence related to transactions often are being performed over a network such as the Internet. In addition, the price or rent of a residence is determined by factors such as the area of the property, the layout, the floor number, the directions in which rooms face, the management status, location conditions, the shape of the plot of land, and the prices of nearby properties.

CITATION LIST

Patent Literature

Patent Literature 1: JP 2009-098446A

DISCLOSURE OF INVENTION

Technical Problem

However, when deciding the price/rent of a residence or when deciding whether to buy/rent, what kind of people the surrounding residents are is not considered. For example, Patent Literature 1 discloses a system able to detect and manage the degree to which people are gathered at respective positions (locations), and provide conditions in which people are gathered incidentally to a user as cluster information. Such a system is also capable of sensing the biological conditions of gathered people, and thereby extract locations where people corresponding to a specific psychological state are gathered. However, the system according to Patent Literature 1 is for knowing some kind of occurrence (such as an event) happening incidentally at that location, and the outputting of what kind of people the surrounding residents are is not considered.

For example, in the case of newly buying/renting a residence, if the realities of a region could be ascertained, such as the state of health and degree of positivity of the surrounding residents, property searching with a higher degree of satisfaction could be conducted. Likewise, when deciding the price/rent of a residence, if the realities of a region could be ascertained, such as the state of health and degree of positivity of the surrounding residents, a more appropriate value could be decided.

Accordingly, the present disclosure proposes an information processing device, an information processing method, and a program capable of providing property transactions with a higher degree of satisfaction by generating certain property information using a happiness score based on user information.

Solution to Problem

According to the present disclosure, there is provided an information processing device including: a computation unit that computes a happiness score on a basis of sensed user information; and a generation unit that generates certain property information using the computed happiness score.

According to the present disclosure, there is provided an information so processing method that is executed by a processor, the information processing method including: computing a happiness score on a basis of sensed user information; and generating certain property information using the computed happiness score.

According to the present disclosure, there is provided a program causing a computer to function as: a computation unit that computes a happiness score on a basis of sensed user information; and a generation unit that generates certain property information using the computed happiness score.

Advantageous Effects of Invention

According to the present disclosure as described above, by generating certain property information using a happiness score based on user information, it becomes possible to provide property transactions with a higher degree of satisfaction.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 5 is a diagram illustrating an example of a search parameter input screen during a property search displayed in the present embodiment.

FIG. 6 is a diagram illustrating an example of a property information presentation screen displayed in the present embodiment.

FIG. 7 is a diagram illustrating an example of a property information presentation screen displayed in the present embodiment.

FIG. 8 is a diagram illustrating an example of a property information settings screen displayed in the present embodiment.

FIG. 9 is a diagram illustrating an example of a property recommendation information presentation screen displayed in the present embodiment.

FIG. 11 is a block diagram illustrating an example hardware configuration of an information processing device according to an embodiment of the present disclosure.

MODE(S) FOR CARRYING OUT THE INVENTION

Figure 1:
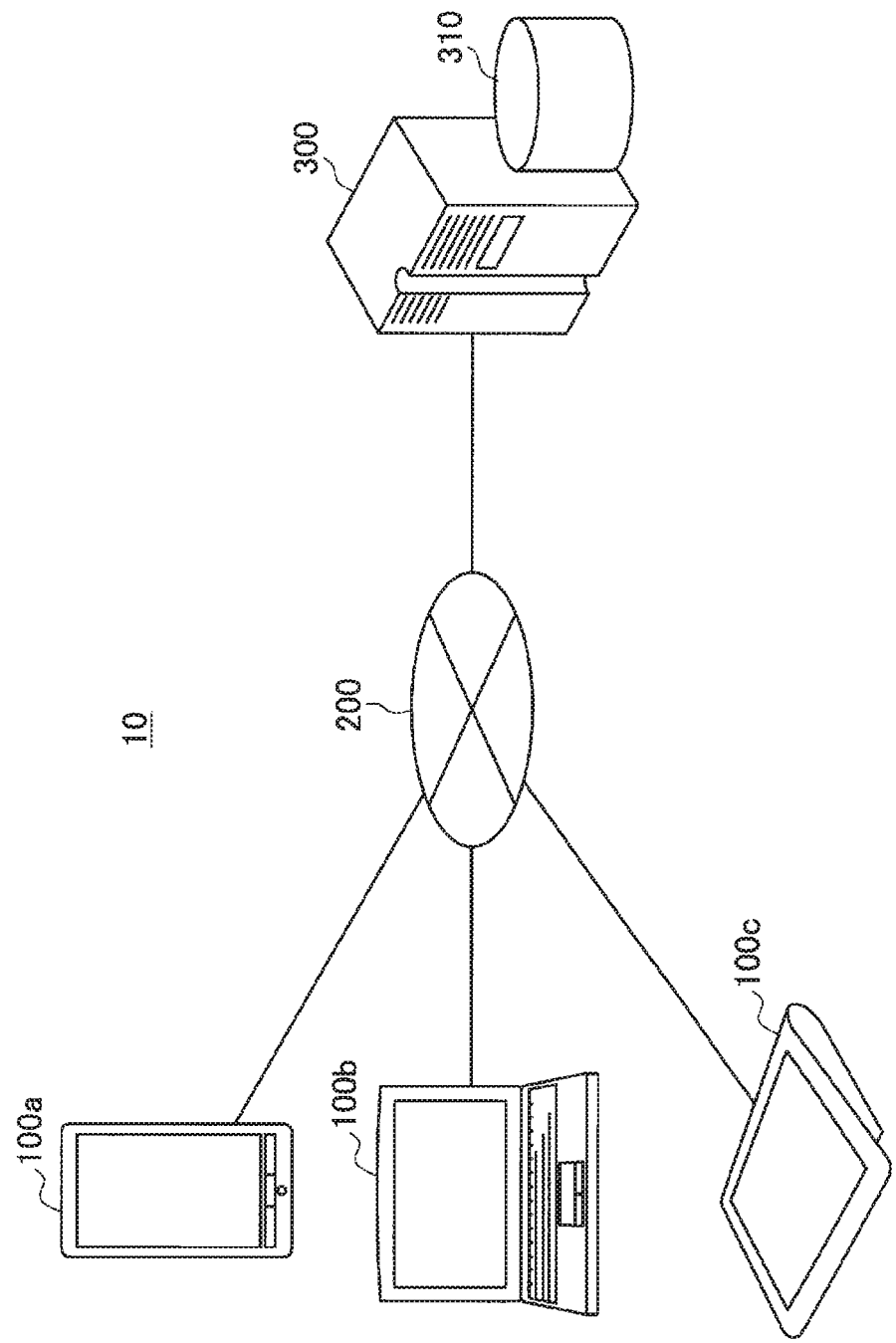
FIG. 1 is a diagram illustrating a diagrammatic configuration of a system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. Summary of system according to an embodiment of the present disclosure
   1-1. Client configuration
   1-2. Server configuration
2. Functional configuration
3. Property information presentation process
4. Property information presentation screen examples
5. Hardware configuration
6. Conclusion

1. Diagrammatic Configuration of a System According to an Embodiment of the Present Disclosure FIG. 1 is a diagram illustrating a diagrammatic configuration of a system according to an embodiment of the present disclosure. Referring to FIG. 1, a system 10 according to the present embodiment includes a client 100 and a server 300. The client 100 and the server 300 are connected by a network 200, and are able to communicate with each other.

The client 100 may include devices such as a smartphone 100a, a personal computer 100b, and a tablet 100c, for example. The client 100 is not limited to the illustrated example, and may include any type of terminal device having a function of inputting and outputting information with respect to a user. To output information to a user, the client 100 uses images, sound, and the like, for example. Additionally, the client 100 may accept the input of information from the user through operating input on the terminal device, sound indicating speech, an image indicating a gesture or line of sight, or the like.

The server 300 includes one or multiple server devices on a network. In the case of realizing the functions of the server 300 described hereinafter by having multiple server devices act cooperatively, the totality of the multiple server devices may be treated as a single information processing device. Alternatively, at least some of the server devices may be run by an operator different from the operator of the server 300 described hereinafter. In such a case, in the following description, part of the server 300 may be referred to as an external server not included in the system 10. In the present embodiment, at least one or some of the server devices include a database 310. The database 310 stores information related to real estate and transaction histories thereof.

The network 200 includes any of various types of wired or wireless networks, such as the Internet, a local area network (LAN), or a mobile phone network, for example. The network 200 connects the client 100 and the server 300, and may also connect multiple server devices included in the server 300. In cases in which multiple types of networks are included in the network 200, the network 200 may also include devices such as routers and hubs that interconnect such networks.

Figure 2:
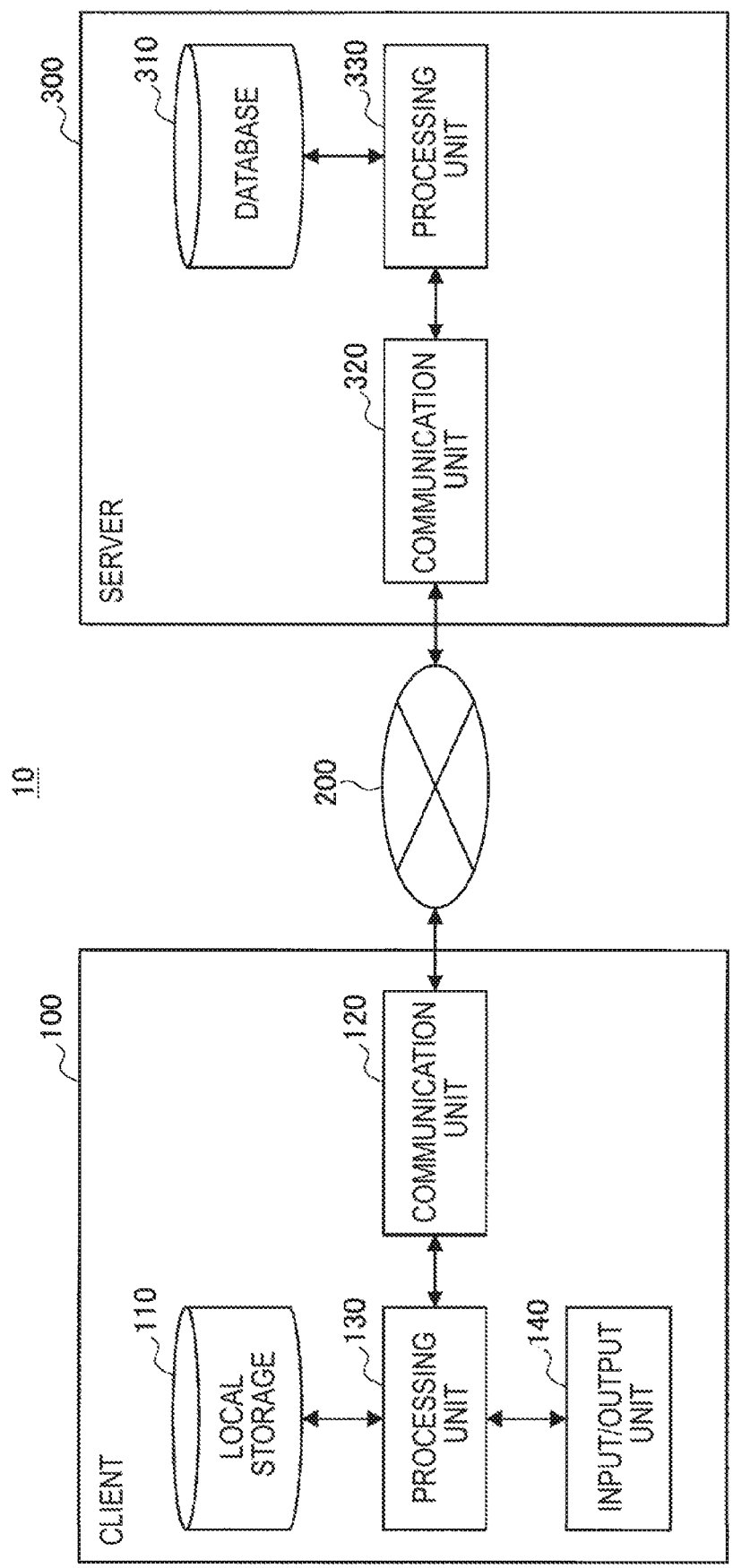
FIG. 2 is a block diagram illustrating an internal configuration of a system according to an embodiment of the present disclosure.

FIG. 2 is a block diagram illustrating an internal configuration of a system according to an embodiment of the present disclosure. Referring to FIG. 2, the client 100 may include local storage 110, a communication unit 120, a processing unit 130, and an input/output unit 140. The server 300 may include the database 310, a communication unit 320, and a processing unit 330. Hereinafter, each of the functional elements will be described further. Note that the terminal device that functions as the client 100, and the one or multiple server devices included in the server 300, are realized by the hardware configuration of the information processing device described later, for example.

<1-1. Client Configuration>

The local storage 110 is realized by memory or storage included in the terminal device, for example. In the local storage 110, information provided by the server 300 over the network 200 and information input by the user through the input/output unit 140 is stored temporarily or persistently, for example. The user utilizes the information stored in the local storage 110 to reference information provided by the server 300 even while offline, or to input a draft of information to provide to the server 300.

The communication unit 120 communicates with the server 300 over the network 200. The communication unit 120 is realized, for example, by a communication device that executes communication on a network to which the client 100 is connected.

The processing unit 130 is realized by a processor such as a central processing unit (CPU) included in the terminal device, for example. For example, the processing unit 130 executes a process of requesting information from the server 300 through the communication unit 120, based on information input by the user through the input/output unit 140. As another example, the processing unit 130 executes a process of outputting information to the user through the input/output unit 140, based on information provided by the server 300 through the communication unit 120. At this point, the processing unit 130 may also execute a process of converting provided information into a suitable format according to the type of the input/output unit 140.

The input/output unit 140 is realized by an input device, such as a touch panel, mouse, keyboard, microphone, or camera (imaging device), and an output device, such as a display or speaker, included in the terminal device, for example. Note that the input/output unit 140 may also include only one of either an input device or an output device. For example, information received from the server 300 through the communication unit 120 is processed by the processing unit 130 and displayed on a display included in the input/output unit 140. As another example, user operating input acquired by a touch panel or the like included in the input/output unit 140 is processed by the processing unit 130 and transmitted to the server 300 through the communication unit 120.

Since the functions themselves of the processing unit 130 and the input/output unit 140 as above are similar to the functions of a processing unit and an input/output unit in a typical terminal device, for example, a detailed explanation thereof may be reduced or omitted in the following description of the present embodiment. However, even in such cases, if the information received from the server 300 is characteristic, for example, the functions of the processing unit 130 or so the input/output unit 140 in the client 100 with respect to processing and outputting such information may also be characteristic compared to these functions in a typical terminal device.

<1-2. Server Configuration>

The database 310 is realized by memory or storage included in the server device, for example. As described earlier, in the database 310, information related to real estate and transactions thereof is stored. Also, in the database 310, information related to a user of the client 100 may also be stored. Note that more specific types of information stored in the database 310 may differ depending on the content of the service provided by the server 300.

The communication unit 320 communicates with the client 100 over the network 200. Additionally, the communication unit 320 may also communicate with an external server over the network 200. The communication unit 320 is realized by a communication device that executes communication on a network, for example, to which the server 300 is connected.

The processing unit 330 is realized by a processor such as a CPU included in the server device, for example. For example, the processing unit 330 executes a process of acquiring information from the database 310 based on information received from the client 100 through the communication unit 320, and after processing the acquired information as necessary, transmitting to the client 100 through the communication unit 320.

Note that if the server 300 includes multiple server devices, the functional configuration of the server 300 described above may be realized distributed among the multiple server devices. For example, the functions of the database 310 may be realized by being concentrated in one of the server devices, or may be realized by centrally operating and managing a database distributed among multiple server devices. As another example, the functions of the processing unit 330 may also be so realized by centrally operating and managing a processor distributed among multiple server devices. In this case, the functions of the processing unit 330 described hereinafter may be realized by being distributed serially or in parallel among multiple server devices, regardless of the demarcations of the function blocks defined for the sake of explanation.

2. Functional Configuration

Next, a functional configuration of the database 310 and the processing unit 330 of the server 300 will be described with reference to FIG. 3.

Figure 3:
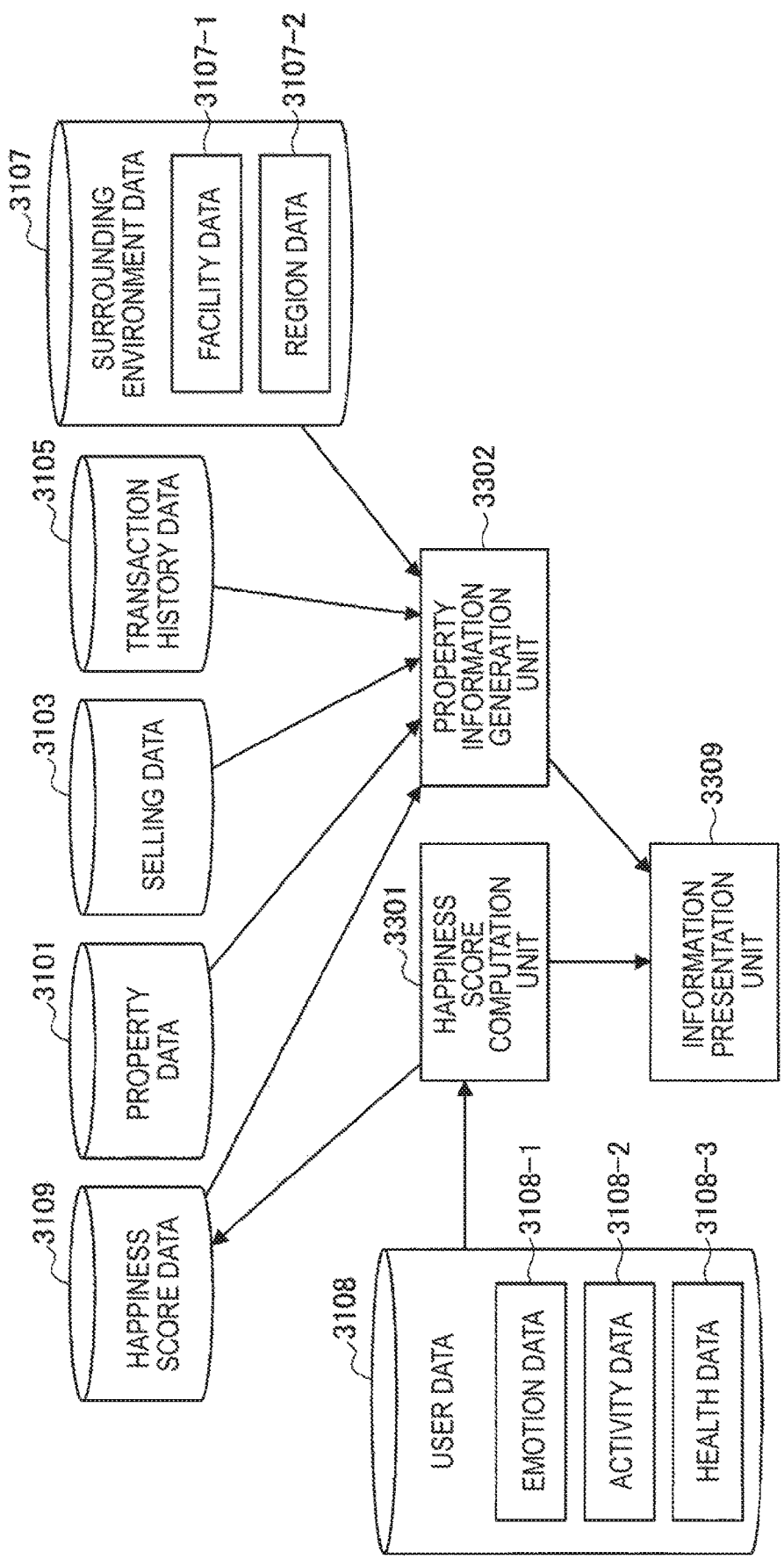
FIG. 3 is a block diagram illustrating an exemplary functional configuration of a database and a processing unit of a server according to an embodiment of the present disclosure.

FIG. 3 is a block diagram illustrating an exemplary functional configuration of a database and a processing unit of a server according to an embodiment of the present disclosure. The diagram illustrates, as functions of the database 310 of the server 300, property data 3101, selling data 3103, transaction history data 3105, surrounding environment data 3107, user data 3108, and happiness score data 3109. Additionally, the diagram illustrates, as functions of the processing unit 330, a happiness score computation unit 3301, a property information generation unit 3302, and an information presentation unit 3309. Hereinafter, each of the structural elements will be described further.
<2-1. Exemplary Configuration of Database>
(Property Data 3101)

The property data 3101 functions as master data of real estate properties handled by the service provided by the server 300. The real estate properties may include any of various types of properties, such as land, freestanding buildings, apartments, town houses, and commercial properties, for example. In the property data 3101, data related to these types of real estate properties is registered in association with an ID unique to each property, for example. More specifically, for example, data related to a piece of land may include information such as the type of property, the location, and the ground area. Data related to a building additionally may include information such as the floor area, the room arrangement, facilities, the construction date, the direction of openings, and the lighting state. Furthermore, the data may also include images of features such as the exterior and interior of the property, or the view from the property. If a building has been rebuilt or renovated, for example, data associated with a new ID may be added as a separate property, or a history of the rebuilding, renovation, or the like may be included in the property data 3101.

The selling data 3103 includes data related to the selling currently in progress of real estate properties registered in the property data 3101. More specifically, the selling data 3103 stores data such as the property ID, the selling date, the selling price (including a history of changes), the reason for selling, the current owner, the agent responsible for selling, and introductory text created by the owner or the agent at the time of selling. In the present embodiment, the selling data 3103 stores data related to properties currently for sale. The selling data 3103 is unique with respect to the selling organization and the property ID (for example, if the same property is being sold in parallel by multiple agents, multiple sets of selling data 3103 may be created for each agent with respect to the same property ID). Further, if a transaction is established for a property being sold, some or all of the selling data 3103 for that property is moved to the transaction history data 3105.
(Transaction History Data 3105)

The transaction history data 3105 includes data related to transactions established for real estate properties registered in the property data 3101. More specifically, the transaction history data 3105 stores data such as the transaction ID, the property ID, the selling date, the contract date, the selling price (including a history of changes), the contract price, the reason for selling, the seller (old owner), the buyer (new owner), the agents on the seller side and the buyer side, and introductory text created by the owner or the agent at the time of selling. As described already, the transaction history data 3105 may also be generated on the basis of the selling data 3103 of a property for which a transaction has been established. Alternatively, the transaction history data 3105 may be generated by so importing data about a transaction history provided by a service (including public services) provided by an external server. Whereas the selling data 3103 is unique with respect to the property ID as above, in the transaction history data 3105, multiple sets of data may exist with respect to a single property ID, if the property is one for which transactions have been established multiple times in the past. Consequently, to identify each transaction uniquely as above, a separate transaction ID may also be set in the transaction history data 3105.
(Surrounding Environment Data 3107)

The surrounding environment data 3107 (facility data 3107-1 and region data 3107-2) includes data related to the surrounding environment of real estate properties registered in the property data 3101. For example, the facility data 3107-1 includes data related to various types of facilities located in the vicinity of the real estate property. In this case, the facility data 3107-1 may include information such as a facility's position information, type, name, and opening/closing dates. The facilities include, for example, transportation facilities such as train stations, shops, evacuation facilities, parks, medical institutions, and schools. Also, for example, the region data 3107-2 may include data related to regions where a property is located.
(User Data 3108)

The user data 3108 (emotion data 3108-1, activity data 3108-2, and health data 3108-3) includes data (user data) related to the emotions, activities, and states of health of many users sensed by various sensors. User data is sensed by various sensors provided in an information processing terminal worn or carried by a user (such as a wearable terminal, a smartphone, a mobile phone, or a PC), for example, and is transmitted to the 300.

More specifically, the emotion data 3108-1 may be estimated from at least one of biological information such as brain waves, heart rate, perspiration, blood pressure, and body temperature obtained from various biosensors, speech content and so intensity, intonation, and the like of uttered speech obtained from a microphone, and a facial expression or the like obtained from a camera, for example. Additionally, the emotion data 3108-1 may also be acquired by having a user input/select a current emotion manually from a user interface (UI) screen displayed on the information processing terminal on the user side.

Meanwhile, the activity data 3108-2 may be estimated from at least one of position information, acceleration, angular velocity, and attitude or the like obtained from a position sensor such as a Global Positioning System (GPS) sensor, an acceleration sensor, a gyro sensor, a geomagnetic sensor, or the like. Additionally, the activity data 3108-2 may also be acquired by having a user input/select a current activity manually from a user interface (UI) screen displayed on the information processing terminal on the user side.

Meanwhile, the health data 3108-3 may be estimated from at least one of a bodyweight, blood pressure, heart rate, perspiration, body temperature, number of steps, caloric expenditure, sleeping time, or the like obtained from various sensors such as a bodyweight scale, a blood pressure gauge, a heart rate meter, a perspiration meter, a thermometer, an activity meter, or the like. Additionally, the health data 3108-3 may also be acquired by having a user input/select a current state of health manually from a user interface (UI) screen displayed on the information processing terminal on the user side.

The emotion data 3108-1, the activity data 3108-2, and the health data 3108-3 described above are stored in association with user position information acquired together with the various sensor values. The user position information may be acquired from a position sensor such as a GPS sensor provided in the information processing terminal on the user side, or by having the user input/select a position from a UI screen. Note that the position information associated with the emotion data 3108-1, the activity data 3108-2, and the health data 3108-3 is not limited to the user's current position information at the time of sensing, and may also be the user's place of residence. Also, the process of estimating emotion data 3108-1, the activity data 3108-2, and health data 3108-3 based on various sensor values may be conducted by the information processing terminal on the user side, by the processing unit 330 of the server 300, or by another processing server (not illustrated).

(Happiness Score Data 3109)

The happiness score data 3109 includes data related to the happiness of people (for example, residents) in respective positions (such as regions). The happiness score data 3109 may be computed on the basis of the user data 3108 by the happiness score computation unit 3301, and stored in association with position information.

<2-2. Exemplary Configuration of Processing Unit>
(Happiness Score Computation Unit 3301)

The happiness score computation unit 3301 computes a happiness score for each position, on the basis of the user data 3108 (emotion data 3108-1, activity data 3108-2, and health data 3108-3) associated with the position information. For example, the happiness score computation unit 3301 may compute a happiness score for each position on the basis of positive emotion data from among the emotion data 3108-1, or compute a happiness score for each position on the basis of positive activity data from among the activity data 3108-2. Additionally, the happiness score computation unit 3301 may also compute a happiness score for each position on the basis of positive health data from among the health data 3108-3. Positive emotion data corresponds to emotions such as joy, delight, gratitude, serenity, curiosity, hope, pride, and love, for example. Also, positive activity data corresponds to activities such as going out during the day, taking exercise such as walking or running, and having a settled life rhythm (regular habits), for example. Also, positive health data corresponds to having appropriate values of factors such as bodyweight, blood pressure, perspiration, body temperature, number of steps, caloric expenditure, and sleeping time, being less susceptible to diseases or common colds, having a high degree of concentration towards things, having a low level of stress, so and the like, for example.

In addition, the happiness score computation unit 3301 is also able to compute a happiness score for each position on the basis of positive emotion data, positive activity data, and positive health data. More specifically, for example, a score $S_e$ expressing the degree of positivity in emotion at a certain position can be computed according to Formula 1 below, provided that $E_i$ {i=0, . . . , n} is a recognizable emotion, $C_{Ei}$ is a count of the emotion $E_i$ recognized at the certain position over a fixed period, and $W_{Ei}$ is a weighting of the degree of positivity with respect to the emotion $E_i$, for example.

[Math. 1]

$$S_e = \Sigma_{i=0}^{n}(C_{Ei} \times W_{Ei}) \quad \text{Formula 1}$$

Also, a score $S_a$ expressing the degree of positivity in activity at a certain position can be computed according to Formula 2 below, provided that $A_i$ {i=0, . . . , n} is a recognizable activity, $C_{Ai}$ is a count of the activity $A_i$ recognized at the certain position over a fixed period, and $W_{Ai}$ is a weighting of the degree of positivity with respect to the activity $A_i$ for example.

[Math. 2]

$$S_a = \Sigma_{i=0}^{n}(C_{Ai} \times W_{Ai}) \quad \text{Formula 2}$$

Also, a score $S_h$ expressing the degree of positivity in health at a certain position can be computed according to Formula 3 below, provided that $H_i$ {i=0, . . . , n} is a recognizable health factor, $Ci_n$ is a count of $H_i$ with a value stipulated to be satisfactory recognized at the certain position over a fixed period, and $W_{Hi}$ is a weighting of the degree of positivity with respect to the health factor $H_i$, for example.

[Math. 3]

$$S_h = \Sigma_{i=0}^{n}(C_{Hi} \times W_{Hi}) \quad \text{Formula 3}$$

Additionally, a happiness score S at a certain position can be computed according to Formula 4 below, provided that $W_e$, $W_a$, and $W_h$ are respective weightings on each of the degrees of positivity $S_e$, $S_a$, and $S_h$ computed above, for example.

[Math. 4]

$$S = S_e \times W_e + S_a \times W_a + W_h \times S_h \quad \text{Formula 4}$$

Note that the values of the weightings $W_e$, $W_a$, and $W_h$ on each of the degrees of positivity in emotion, activity, and health may also be modified (personalized) for individuals seeking to buy/rent a property. With this arrangement, it is possible to compute a happiness score matched to the preferences of the individual seeking to buy/rent a property.

(Property Information Generation Unit 3302)

The property information generation unit 3302 generates certain property information using the happiness score data 3109 computed by the happiness score computation unit 3301. At this time, the property information generation unit 3302 may use data such as the property data 3101, the selling data 3103, the transaction history data 3105, or the surrounding environment data 3107 as necessary.

More specifically, for example, the property information generation unit 3302 generates property information in which information about one or more properties matching a search condition specified by the buyer/renter in a property transaction is arranged in order of the happiness score around the location of each property. The property information generation unit 3302 may also generate property information matching the search condition, and property information including a happiness score around the location of each property. The property information generation unit 3302 may also generate property information in which information about one or more properties matching a search condition specified by the buyer/renter in a property transaction is indicated on a map together with the happiness score around the location of each property. The property information generation unit 3302 may also generate property information indicating information about one or more properties matching the search condition on a map with a superimposed heat map of the happiness score for the region. The property information generation unit 3302 may also generate property information that includes information about one or more properties matching a search condition specified by the buyer/renter in a property transaction, and property information in another region associated with a happiness score similar to the happiness score around the location of each property. The property information generation unit 3302 may also generate property recommendation information for buying/renting, on the basis of the happiness score around the location of each property. The property information generation unit 3302 may also generate property information that includes a property purchase/rental price set on the basis of the happiness score around the location of each property.

(Information Presentation Unit 3309)

The information presentation unit 3309 presents the property information generated by the property information generation unit 3302 to a user through the client 100. More specifically, the information presentation unit 3309 generates data for outputting an image to a display included in the input/output unit 140 of the client 100, and causes the generated data to be transmitted from the communication unit 320 to the client 100. Note that the method of outputting information to the client 100 is not limited to image display. For example, audio output may be adopted so instead of, or in addition to, image display.

The above thus describes a functional configuration of the database 310 and the processing unit 330 of the server 300 according to the present embodiment.

3. Property Information Presentation Process

Next, the flow of a property information presentation process according to the present embodiment will be described specifically with reference to FIG. 4.

Figure 4:
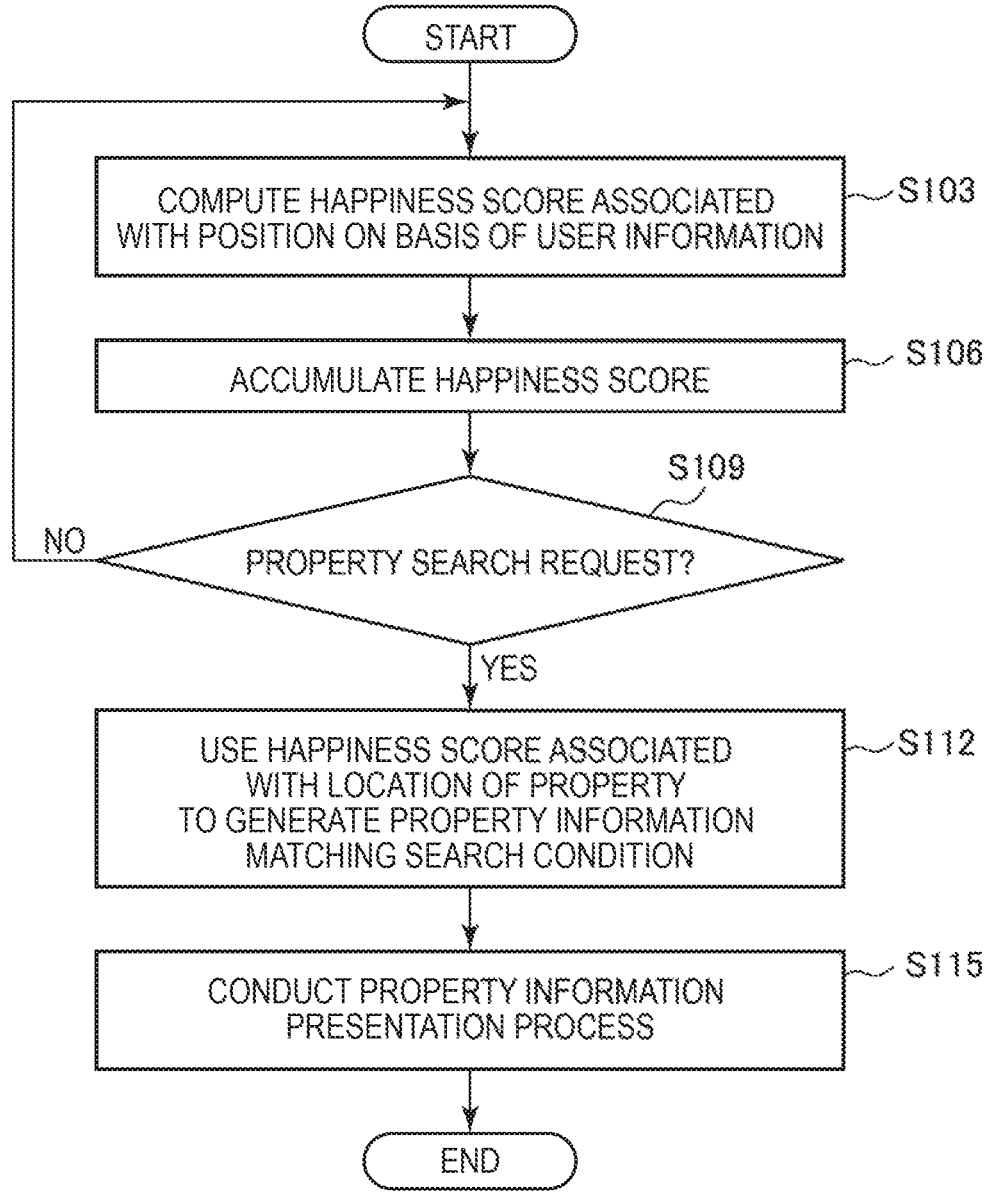
FIG. 4 is a flowchart illustrating a property information presentation process according to the present embodiment.

FIG. 4 is a flowchart illustrating a property information presentation process according to the present embodiment. As illustrated in FIG. 4, first, in step S103, the happiness score computation unit 3301 included in the processing unit 330 of the server 300 uses the user data 3108 to compute the happiness score at a certain position.

Next, in step S106, the happiness score computation unit 3301 accumulates the computed happiness score in the database 310. The above steps S103 and S106 are repeated continually.

Next, in the case of a property search request from the client 100 (S109/Yes), in step S112, the property information generation unit 3302 uses the happiness score associated with the location of the property. For example, the property information generation unit 3302 may generate property information that presents properties matching the search condition in order of the happiness score around the location of each property, property information that presents properties matching the search condition together with the happiness score, or property information that overlays icons of properties matching the search condition on top of a heat map color-coded in accordance with the happiness score.

Subsequently, in step S115, the information providing unit 3309 presents the property information generated by the property information generation unit 3302 to the user through the client 100.

The above thus describes a property information presentation process according to the present embodiment. With this arrangement, during a property search for a real estate transaction, the buyer/renter of a property is able to obtain search results that account for the happiness score of the surrounding region or ascertain the happiness score around a property, and conduct property searching with a higher degree of satisfaction. Note that the order of the processes illustrated in FIG. 4 is one example. For example, the server 300 may also perform the computation of the happiness score of a region included in the search condition when there is a property search request (in other words, the processes in S103 and S106 may be conducted after "S109/Yes").

4. Property Information Presentation Screen Examples

Next, an example of information presented in an embodiment of the present disclosure will be described with reference to an example of a screen displayed on a display included in the input/output unit 140 of the client 100, for example. Note that in the following description, an example of information presented when conducting a transaction for a rental property (such as an apartment or high-rise unit) is described, but information may be presented similarly when selling a property other than a rental property, such as the sale of a condominium, a freestanding building, or land, for example. Also, in the example of information presented when conducting a transaction for a rental property, rental data is stored in the database 310 instead of the selling data 3103, for example.

FIG. 5 is a diagram illustrating an example of a search parameter input screen during a property search displayed in the present embodiment. In the illustrated example, on a screen 1110, a rent condition input field 1110, a property type condition input field 1120, a layout condition input field 1130, an exclusively-owned area condition input field 1140, and a happiness score condition input field 1150 are displayed, and "Happiness Score" is usable as a property search condition. In this case, the property information generation unit 3302 included in the processing unit 330 of the server 300 searches rental data (not illustrated) for properties matching the search condition including the happiness score, and generates property information of the search results. In this way, by specifying the happiness score as a search condition, the property renter is able to search efficiently for properties for which the surrounding happiness is at least a certain level.

Note that in the present embodiment, even in cases in which a happiness score is not specified (or cannot be specified) as a search condition, it is still possible to generate property information that presents properties with a high happiness score from among the properties matching a condition. In this case, the happiness score may or may not be presented on the search results screen.

FIG. 6 is a diagram illustrating an example of a property information presentation screen displayed in the present embodiment. In the illustrated example, property information indicating information about properties matching a search condition (that is, search results) are displayed on a screen 1200. Herein, as an example, the happiness score associated with the position (or surrounding region) indicated by the address of each property is also displayed as property information in the search results. With this arrangement, the property renter is able to recognize the happiness score of each property. Also, on the screen 1200, the happiness score 1210 of the property on the first row is "91", the happiness score 1220 of the property on the second row is "81", and the happiness score 1230 of the property on the third row is "72", with the properties being arranged and displayed in order of highest happiness score. With this arrangement, the property renter is able to preferentially view properties with high happiness scores.

FIG. 7 is a diagram illustrating an example of a property information presentation screen displayed in the present embodiment. In the illustrated example, on a screen 1300, icons 1310, 1320, 1330, and 1340 indicating properties matching a search condition are displayed overlaid onto a map. Also, a heat map 1360 so corresponding to the height of the happiness score is superimposed onto the map on the screen 1300. With this arrangement, the property renter is able to intuitively ascertain which places on the map have a high level of happiness. Note that, as an example, the heat map 1360 illustrated in the diagram expresses locations where the value of the happiness score is equal to or greater than a certain value (for example, the value of a happiness score specified by the property renter as a search condition) with different colors or the like depending on the score, and expresses locations where the value of happiness score falls below the certain value with the same color or the like.

Additionally, if the icon 1310, 1320, 1330, or 1340 indicating a property is selected, detailed information about the relevant property is displayed. At this time, the happiness score may also be displayed as part of the detailed information about the property, as illustrated in the diagram.

FIG. 8 is a diagram illustrating an example of a property information setting screen displayed in the present embodiment. In the illustrated example, input fields enabling a property lender to input information related to a rental property (such as the rental property ID, the property name, the address, the rental fee, the exclusively-owned area, and the layout) are displayed on a screen 1400. At this point, a surrounding happiness score 1410 is displayed automatically in accordance with the input address. With this arrangement, the property lender is able to decide a rental fee 1420 appropriately by referencing the happiness score 1410 around the property. Note that a rental fee 1420 computed on the server 300 side onto the happiness score 1410 and other property information may also be presented.

Note that on the property information setting screen, it is also possible to set locations at which to put out advertisements. For example, in a case of putting out advertisements for the rental property through an intermediary real estate business (agent), which real estate businesses in which regions to request may be set. To the property lender, which region to put out advertisements in is also important for so raising the price and successful contract probability of one's own property. At this point, in the present embodiment, it is possible to set locations at which to put out advertisements by referencing the happiness score. For example, the property information generation unit 3302 matches the happiness score of the rental property with the happiness score of the locations of real estate shops in the surrounding region, and generates information recommending real estate shops at locations having a similar degree of happiness score as locations at which to put out advertisements. This is because by putting out advertisements in regions where there are many people with the same degree of happiness score, a higher price and successful contract probability for the rental property can be expected.

In addition, in the present embodiment, it is also possible for the property information generation unit 3302 to generate and present to the property renter recommendation information using the happiness score. Hereinafter, the presentation of recommendation information will be described with reference to FIGS. 9 and 10.

FIG. 9 is a diagram illustrating an example of a property recommendation information presentation screen displayed in the present embodiment. In the illustrated example, property information 1510, 1520, and 1530 related to properties having a happiness score close to a selected property (not illustrated) is displayed as recommendation information on a screen 1500. The screen 1500 may be displayed in part of the screen when a property renter has selected one property from among multiple properties presented as illustrated in FIG. 6 and is viewing detailed information, for example. In this way, by recommending other properties having a happiness score of similar degree to a selected property when viewing the selected property, the choice of properties increases, and the property renter is able to conduct property searching with a higher degree of satisfaction. Additionally, the property information generation unit 3302 may also generate property recommendation information recommending a property which matches a condition other than happiness score from among search conditions set by the property rent, and which so has a high happiness score, and cause the information presentation unit 3309 to present the generated property recommendation information on the client 100.

Figure 10:
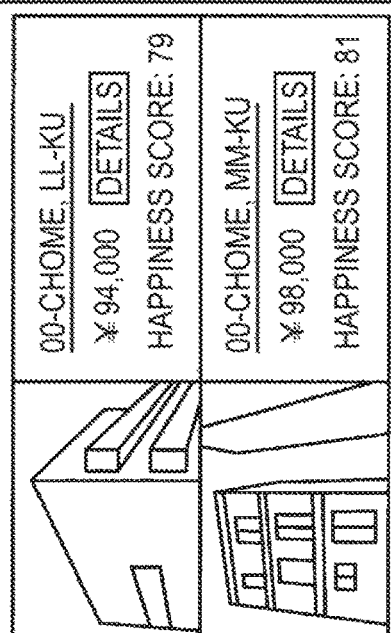
FIG. 10 is a diagram illustrating an example of a property recommendation information presentation screen displayed in the present embodiment.

FIG. 10 is a diagram illustrating an example of a property recommendation information presentation screen displayed in the present embodiment. In the illustrated example, a web page viewed by a property renter, and property information 1610 related to properties having a happiness score of a similar degree as a property previously referenced by the property renter, or to properties having a happiness score that match a previously set search condition, are displayed on a screen 1600. In this way, when the property renter views a web page on the client 100, by display as advertisements property recommendation information generated using the happiness score, the advertising effectiveness for real estate transactions can be improved.

In addition, the property information generation unit 3302 is also capable of generating property recommendation information by using a profile of the property buyer/renter (such as hobbies and interests, gender, age, family structure, and behavioral patterns). For example, the property information generation unit 3302 uses at least one of the emotion data 3108-1, the activity data 3108-2, and the health data 3108-3 to generate property recommendation information recommending a property or region in a location containing many people with features similar to the property buyer/renter. For example, in a case in which "running" is a hobby of the property buyer/renter, properties in a region containing many people with similar hobbies can be recommended on the basis of the activity data 3108-2. With this arrangement, the property buyer/renter is able to conduct property searching with a higher degree of satisfaction.

5. Hardware Configuration

Next, with reference to FIG. 11, a hardware configuration of an information processing device according to an embodiment of the present disclosure is described. FIG. 11 is a block diagram illustrating a hardware configuration example of the information processing device according to the embodiment of the present disclosure. An illustrated information processing device 900 may achieve the server 300 or the client (100 in the above described embodiment.

The information processing device 900 includes a central processing unit (CPU) 901, read only memory (ROM) 903, and random access memory (RAM) 905. In addition, the information processing device 900 may include a host bus 907, a bridge 909, an external bus 911, an interface 913, an input device 915, an output device 917, a storage device 919, a drive 921, a connection port 923, and a communication device 925. The information processing device 900 may include a processing circuit such as a digital signal processor (DSP), an application-specific integrated circuit (ASIC), or a field-programmable gate array (FPGA), instead of or in addition to the CPU 901.

The CPU 901 functions as an arithmetic processing device and a control device, and controls the overall operation or a part of the operation of the information 16 processing device 900 according to various programs recorded in the ROM 903, the RAM 905, the storage device 919, or a removable recording medium 927. The ROM 903 stores programs, operation parameters, and the like used by the CPU 901. The RAM 905 transiently stores programs used when the CPU 901 is executed, and parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may be a remote control device that uses, for example, infrared radiation and another type of radio waves. Alternatively, the input device 915 may be an external connection device 929 such as a mobile phone that corresponds to an operation of the information processing device 900. The input device 915 includes an input control circuit that generates input signals on the basis of information which is input by a user to output the generated input signals to the CPU 901. The user inputs various types of data and indicates a processing operation to the information processing device 900 by operating the input device 915.

The output device 917 is realized by a device capable of notifying the user of acquired information using senses such as vision, hearing, and touch. The output device 917 may be a display device such as a liquid crystal display (LCD) or an organic electro-luminescence (EL) display, an audio output device such as one or more speakers or headphones, or a device such as a vibrator. The output device 917 outputs results obtained from processing by the information processing device 900 in the form of visual information such as text or an image, in the form of audio such as speech or sound, or in the form of vibration or the like.

The storage device 919 is a device for data storage that is an example of a storage unit of the information processing device 900. The storage device 919 includes, for example, a magnetic storage device such as a hard disk drive (HDD), a semiconductor storage device, an optical storage device, or a magneto-optical storage device. The storage device 919 stores therein the programs and various data executed by the CPU 901, and various data acquired from an outside.

The drive 921 is a reader/writer for the removable recording medium 927 such as a magnetic disk, an optical disc, a magneto-optical disk, and a semiconductor memory, and built in or externally attached to the information processing device 900. The drive 921 reads out information recorded on the mounted removable recording medium 927, and outputs the information to the RAM 905. The drive 921 writes the record into the mounted removable recording medium 927.

The connection port 923 is a port used to connect devices to the information processing device 900. The connection port 923 may be a Universal Serial Bus (USB) port, an IEEE 1394 port, or a Small Computer System Interface (SCSI) port, for example. The connection port 923 may also be an RS-232C port, an optical audio terminal, a High-Definition Multimedia Interface (HDMI (registered trademark)) port, and so on. The connection of the external connection device 929 to the connection port 923 makes it possible to exchange various kinds of data between the information processing device 900 and the external connection device 929.

The communication device 925 is a communication interface including, for example, a communication device for connection to a communication network 931. The communication device 925 may be a communication card for, for example, a local area network (LAN), Bluetooth (registered trademark), Wi-Fi, or a wireless USB (WUSB). The communication device 925 may also be, for example, a router for optical communication, a router for asymmetric digital subscriber line (ADSL), or a modem for various types of communication. For example, the communication device 925 transmits and receives signals in the Internet or transits signals to and receives signals from another communication device by using a predetermined protocol such as TCP/IP. The communication network 931 to which the communication device 925 connects is a network established through wired or wireless connection. The communication network 931 is, for example, the Internet, a home LAN, infrared communication, radio wave communication, or satellite communication.

The example of the hardware configuration of the information processing device 900 has been described. Each of the structural elements described above may be configured by using a general purpose component or may be configured by hardware specialized for the function of each of the structural elements. The configuration may be changed as necessary in accordance with the state of the art at the time of working of the present disclosure.

6. Conclusion

The embodiments of the present disclosure may include, for example, the above-described information processing apparatus (a server or a client), system, an information processing method executed by the information processing apparatus or the system, a program for causing the information processing device to exhibit its function, and a non-transitory tangible medium having the program stored therein.

In addition, according to the present disclosure described above, by generating certain property information using a happiness score based on user information, it becomes possible to provide property transactions with a higher degree of satisfaction. Namely, regions in which many positive emotions and activities are produced by nearby residents and regions containing many residents in a favorable state of health are considered to be valued more highly by real estate businesses and property buyers/renters than dissimilar regions. Consequently, when determining the price of a property or when deciding a property to buy/rent, by numerically expressing and accounting for such realities of the nearby residents as a "happiness score", property transactions with a higher degree of satisfaction can be conducted.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Additionally, the present technology may also be configured as below.

(1)
An information processing device, including:
a computation unit that computes a happiness score on a basis of sensed user information; and
a generation unit that generates certain property information using the computed happiness score.

(2)
The information processing device according to (1), in which
user position information at a time of sensing is associated with the user information, and
the computation unit computes the happiness score at each position.

(3)
The information processing device according to (2), further including:
a presentation control unit that controls a presentation of the property information generated by the generation unit on a display screen of a client terminal of a party to a property transaction.

(4)
The information processing device according to any one of (2) to (3), in which
the sensed user information includes user emotion information, and
the computation unit computes a happiness score of a region on a basis of positive emotion information accumulated from a plurality of users.

(5)
The information processing device according to (4), in which
the emotion information is acquired on a basis of at least one of user biological information, speech content analyzed from speech information, a feature of uttered speech, facial expression information analyzed from a captured image, and emotion information selected by a user.

(6)
The information processing device according to any one of (2) to (5), in which
the sensed user information includes user activity information, and
the computation unit computes a happiness score of a region on a basis of positive activity information accumulated from a plurality of users.

(7)
The information processing device according to (6), in which
the activity information is acquired on a basis of at least one of user position information, acceleration, and activity information selected by a user.

(8)
The information processing device according to any one of (2) to (7), in which
the sensed user information includes user health information, and
the computation unit computes a happiness score of a region on a basis of positive health information accumulated from a plurality of users.

(9)
The information processing device according to (8), in which
the health information is acquired on a basis of at least one of user biological information, the number of steps, caloric expenditure, and health information selected by a user.

(10)
The information processing device according to any one of (2) to (9), in which
the computation unit computes a happiness score of a region on a basis of positive emotion information, positive activity information, and positive health information accumulated from a plurality of users.

(11)
The information processing device according to any one of (2) to (10), in which
the generation unit generates property information in which information about one or more properties matching a search condition specified by a buyer/renter in a property transaction is arranged in order of the happiness score around a location of each of the properties.

(12)
The information processing device according to (11), in which
the generation unit generates property information matching the search condition, and property information including a happiness score around a location of each property.

(13)
The information processing device according to any one of (2) to (10), in which
the generation unit generates property information in which information about one or more properties matching a search condition specified by a buyer/renter in a property transaction is indicated on a map together with the happiness score around a location of each of the properties.

(14)
The information processing device according to (13), in which
the generation unit generates property information indicating information about one or more properties matching the search condition on a map with a superimposed heat map of the happiness scores for regions.

(15)

The information processing device according to any one of (2) to (14), in which the generation unit generates property recommendation information that includes information about one or more properties matching a search condition specified by a buyer/renter in a property transaction, and property information in another region associated with a happiness score similar to the happiness score around a location of each of the properties.

(16)

The information processing device according to any one of (2) to (15), in which the generation unit generates property recommendation information for buying/renting, on a basis of the happiness score around a location of each property.

(17)

The information processing device according to any one of (11) to (15), in which the search condition includes the happiness score.

(18)

The information processing device according to any one of (2) to (17), in which the generation unit generates property information that includes a property purchase/rental price set on a basis of the happiness score around a location of a property.

(19)

An information processing method that is executed by a processor, the information processing method including:

computing a happiness score on a basis of sensed user information; and generating certain property information using the computed happiness score.

(20)

A program causing a computer to function as:

a computation unit that computes a happiness score on a basis of sensed user information; and a generation unit that generates certain property information using the computed happiness score.

REFERENCE SIGNS LIST 10 system
100 client
200 network
300 server
310 database
3101 property data
3103 selling data
3105 transaction history data
3107 surrounding environment data
3108 user data
3109 happiness score data
320 communication unit
330 processing unit
3301 happiness score computation unit
3302 property information generation unit
3309 information presentation unit

The invention claimed is:

1. An information processing device including a real estate search and presentation system, comprising:

a data collection device configured to collect resident input information from a plurality of residents;

the resident input information including blood pressure data of a resident and GPS position data of the resident and address location of the resident;

a blood pressure sensor configured to sense and provide the blood pressure data of the resident;

a Global Positioning System (GPS) sensor configured to sense and provide the GPS position data of the resident;

a resident input device configured to receive the address location of the resident;

happiness computation circuitry configured to generate a happiness score indicating an emotional happiness assessment associated with the resident in connection with the GPS position data of the resident, and the happiness score generated on the basis of positive emotion data including positive emotion data estimated from biological information including the blood pressure data of the resident;

the happiness score memory configured to store the happiness score in association with the GPS position data of the resident and the address location of the resident, for each of the plurality of residents;

property information memory configured to store a plurality of real estate property information including address location data for each of the plurality of real estate property information;

property information generation circuitry configured to:
  detect when a search request was submitted,
  generate one or more resultant real estate property information including the resultant address location data for each of the resultant real estate property information, wherein each of the resultant real estate property information met criteria of the search request, the criteria including a happiness score criteria, and
  provide a resultant happiness score associated with each resultant address location for each of the resultant real estate property information which met the happiness score criteria of the search request, wherein each of the resultant happiness scores were generated based upon resultant positive emotion data estimated from resultant biological information including the resultant blood pressure data of the resultant resident and the associated resultant retrieved GPS position data; and information presentation circuitry configured to cause a display to present the resultant real estate property information which met the happiness score criteria of the search request;

wherein the information presentation circuitry is further configured to arrange the resultant real estate property information in an order based upon each of their associated resultant happiness scores.

2. The information processing device according to claim 1, wherein the address location of the resident is associated with updated resident input information of the resident or a second resident with the same address location as the resident, and the happiness computation circuitry generates an updated happiness score based upon the updated resident input information.

3. The information processing device according to claim 1, wherein the display is a terminal device and the information processing device is a server and the blood pressure data was obtained from the blood pressure sensor of a device in physical contact with the resident.

4. The information processing device according to claim 1, wherein the happiness computation circuitry generates a region happiness score of a region on a basis of accumulated happiness scores, which were individually generated using the positive emotion data associated with the GPS position data, from a plurality of residents having their address location data determined to be located in the region.

5. The information processing device according to claim 1, wherein
the happiness computation circuitry generates a region happiness score of a region on a basis of accumulated happiness scores, which were individually generated using the positive emotion data associated with the GPS position data, from a plurality of residents having their address location data determined to be located in the region;
wherein
the positive emotion data includes additional positive emotion data additionally acquired via the resident input device receiving a selection indication from the resident.

6. The information processing device according to claim 1, wherein
the resident input information includes additional information of positive activity data, and
the happiness computation circuitry generates a region happiness score of a region on a basis of accumulated happiness scores, which were individually generated using the positive activity data associated with the GPS position data and the positive emotion data associated with the GPS position data, from a plurality of residents having their address location data determined to be located in the region.

7. The information processing device according to claim 1, wherein
the resident input information includes additional information of positive activity data, and
the happiness computation circuitry generates a region happiness score of a region on a basis of accumulated happiness scores, which were individually generated using the positive activity data associated with the GPS position data and the positive emotion data associated with the GPS position data, from a plurality of residents having their address location data determined to be located in the region;
wherein
the positive activity data is acquired via the resident input device receiving an activity selection indication from the resident.

8. The information processing device according to claim 1, wherein
the resident input information includes additional information of positive health data, and
the happiness computation circuitry generates a region happiness score of a region on a basis of accumulated happiness scores, which were individually generated using the positive health data associated with the GPS position data and the positive emotion data associated with the GPS position data, from a plurality of residents having their address location data determined to be located in the region.

9. The information processing device according to claim 1, wherein
the resident input information includes additional information of positive health data, and the happiness computation circuitry generates a region happiness score of a region on a basis of accumulated happiness scores, which were individually generated using the positive health data associated with the GPS position data and the positive emotion data associated with the GPS position data, from a plurality of residents having their address location data determined to be located in the region;
wherein
the positive health data is acquired via the resident input device receiving a health selection indication from the resident.

10. The information processing device according to claim 1, wherein
the resident input information includes additional information of positive activity data and positive health data, and
the happiness computation circuitry generates a region happiness score of a region on a basis of accumulated happiness scores, which were individually generated using the positive activity data associated with the GPS position data and the positive health data associated with the GPS position data and the positive emotion data associated with the GPS position data, from a plurality of residents having their address location data determined to be located in the region.

11. The information processing device according to claim 1, wherein
the resident input information includes additional information of positive activity data and positive health data, and
the happiness computation circuitry generates a region happiness score of a region on a basis of accumulated happiness scores, which were individually generated using the positive activity data associated with the GPS position data and the positive health data associated with the GPS position data and the positive emotion data associated with the GPS position data, from a plurality of residents having their address location data determined to be located in the region;
wherein
the positive activity data is acquired via the resident input device receiving an activity selection indication from the resident and the positive health data is acquired via the resident input device receiving a health selection indication from the resident.

12. The information processing device according to claim 1, wherein
the property information generation circuitry generates, and the information presentation circuitry presents the resultant real estate property information based upon each resultant address location being located within a map area centered around an input search address which was received via the resident input device as part of the criteria of the search request, and each of the resultant real estate property information also met the happiness score criteria.

13. The information processing device according to claim 1, wherein
the property information generation circuitry generates, and the information presentation circuitry presents the resultant real estate property information based upon each resultant address location being located within a map area centered around an input search address which was received via the resident input device as part of the criteria of the search request, and each of the resultant real estate property information also met the happiness score criteria;

wherein
the property information generation circuitry generates, and the information presentation circuitry presents the resultant real estate property information indicating the order as being ordered with a color indication associated with a range of value within which each resultant happiness score falls into.

14. The information processing device according to claim 1, wherein
the information presentation circuitry presents further information for each resultant real estate property information including each of the resultant happiness scores and resultant additional property type information.

15. The information processing device according to claim 1, wherein
the property information generation circuitry generates, and the information presentation circuitry presents the resultant real estate property information indicating the order as being ordered with a color indication associated with a range of value within which each resultant happiness score falls into, wherein
the property information generation circuitry generates, and the information presentation circuitry presents further information of a superimposed heat map of region happiness scores for regions located within a map area, so that the regions are indicated with a color that corresponds to a range of happiness scores, the map area centered around an input search address which was received via the resident input device as part of the criteria of the search request, wherein each of the resultant real estate property information met both the input search address criteria and the happiness score criteria.

16. The information processing device according to claim 1, wherein
the property information generation circuitry generates, and the information presentation circuitry presents the resultant real estate property information including resultant recommended one or more properties matching the criteria of the search request, and the resultant recommended one or more properties have associated address location data located in a recommended geographical region determined to have an accumulated happiness score similar to the happiness score matching the happiness score criteria of the criteria of the search request.

17. The information processing device according to claim 1, wherein
for each of the resultant real estate property information which met the criteria of the search request, the property information generation circuitry generates, and the information presentation circuitry presents: a purchase or rental price.

18. The information processing device according to claim 1, wherein
for each of the resultant real estate property information which met the criteria of the search request, the property information generation circuitry generates, and the information presentation circuitry presents: a purchase or rental price, a distance to a nearest public transportation location, and a property type indication in addition to the presented happiness score.

19. The information processing device according to claim 1, wherein
the happiness computation circuitry is configured to generate the happiness score for each of the GPS position data of the resident on the basis of the positive emotion data including the positive emotion data estimated from the biological information including the blood pressure data of the resident, and from the biological information including at least one of: heart rate or brain waves or perspiration or body temperature obtained from an associated biosensor, and from the biological information including information obtained from audio data or camera data.

20. The information processing device according to claim 1, wherein
the happiness computation circuitry is configured to generate the happiness score for each of the GPS position data of the resident on the basis of the positive emotion data including the positive emotion data estimated from the biological information including the blood pressure data of the resident, and from activity data of at least one of: position or acceleration or angular velocity or altitude, obtained from the GPS sensor, and from health data of at least one of: bodyweight or heart rate or perspiration or body temperature or number of steps or caloric expenditure or sleeping time obtained from an associated device.

* * * * *